United States Patent [19]

Sugita et al.

[11] Patent Number: 5,702,798
[45] Date of Patent: Dec. 30, 1997

[54] COMPOSITE MATERIAL WITH CONTROLLED ELASTICITY

[75] Inventors: Yukio Sugita, Yokohama; Kintaro Aihara, Chiba; Sadayuki Ishiyama, Setagaya-ku; Jun Yamada, Yokohama, all of Japan

[73] Assignee: Nippon Petrochemicals Company, Limited, Tokyo, Japan

[21] Appl. No.: 491,639

[22] Filed: Jun. 19, 1995

[30] Foreign Application Priority Data

Jun. 20, 1994 [JP] Japan ................. 6-160691
Jun. 20, 1994 [JP] Japan ................. 6-160692
Dec. 20, 1994 [JP] Japan ................. 6-334868

[51] Int. Cl.$^6$ ........................ B32B 3/10
[52] U.S. Cl. .............. 428/131; 428/134; 428/135; 428/138
[58] Field of Search .................. 428/252, 286, 428/131, 134, 135, 138

[56] References Cited

U.S. PATENT DOCUMENTS

| | | |
|---|---|---|
| 3,949,129 | 4/1976 | Hubbard . |
| 4,414,970 | 11/1983 | Berry . |
| 4,525,407 | 6/1985 | Ness ........................ 428/138 |
| 5,393,599 | 2/1995 | Quantrille et al. ........... 428/284 |
| 5,447,462 | 9/1995 | Smith et al. ................ 450/122 |

FOREIGN PATENT DOCUMENTS

| | | |
|---|---|---|
| 0 368 516 | 5/1990 | European Pat. Off. . |
| 0 678 607 | 10/1995 | European Pat. Off. . |
| 60-31833 | 2/1985 | Japan . |
| 60-31869 | 2/1985 | Japan . |
| 60-47808 | 3/1985 | Japan . |
| 61-289163 | 12/1986 | Japan . |
| 62-121045 | 6/1987 | Japan . |
| 62-162538 | 7/1987 | Japan . |
| 63-92433 | 4/1988 | Japan . |
| 3-158236 | 7/1991 | Japan . |
| 3-213543 | 9/1991 | Japan . |
| WO 93/15247 | 8/1993 | WIPO . |
| WO 93/15248 | 8/1993 | WIPO . |
| WO 95/29810 | 11/1995 | WIPO . |

*Primary Examiner*—Christopher Raimund
*Attorney, Agent, or Firm*—Scully, Scott, Murphy & Presser

[57] ABSTRACT

A controlled elastic composite material which is produced by forming a flexible elastomer layer or layers on one or both surfaces of at least one member selected from the group consisting of (a) a longitudinally monoaxially oriented reticular web, (b) a transversally monoaxially oriented reticular web, (c) a woven or non-woven fabric composed of monoaxially oriented tapes, and (d) a stretched long fiber web in which long fibers are aligned almost in one direction.

15 Claims, 6 Drawing Sheets

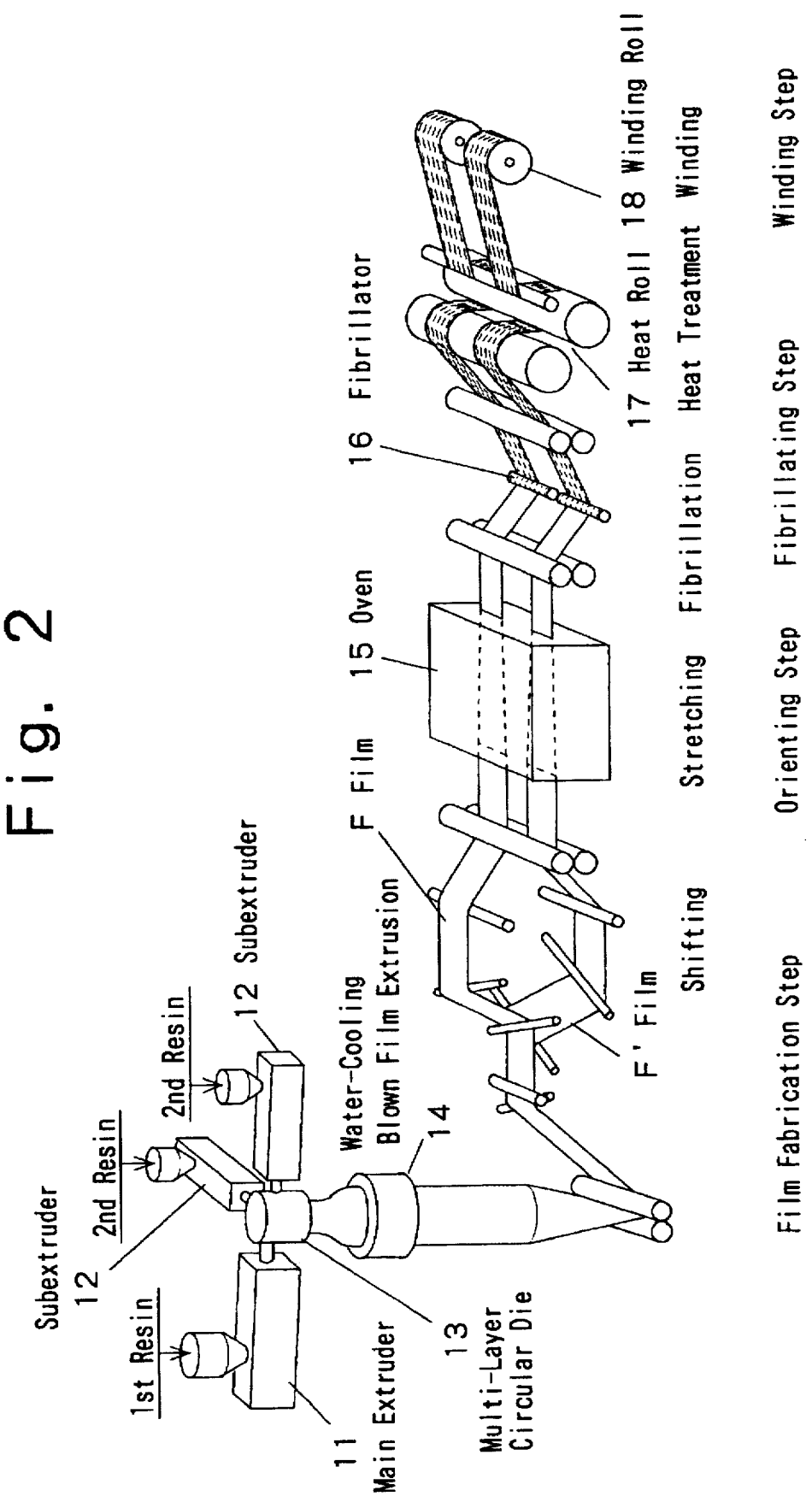

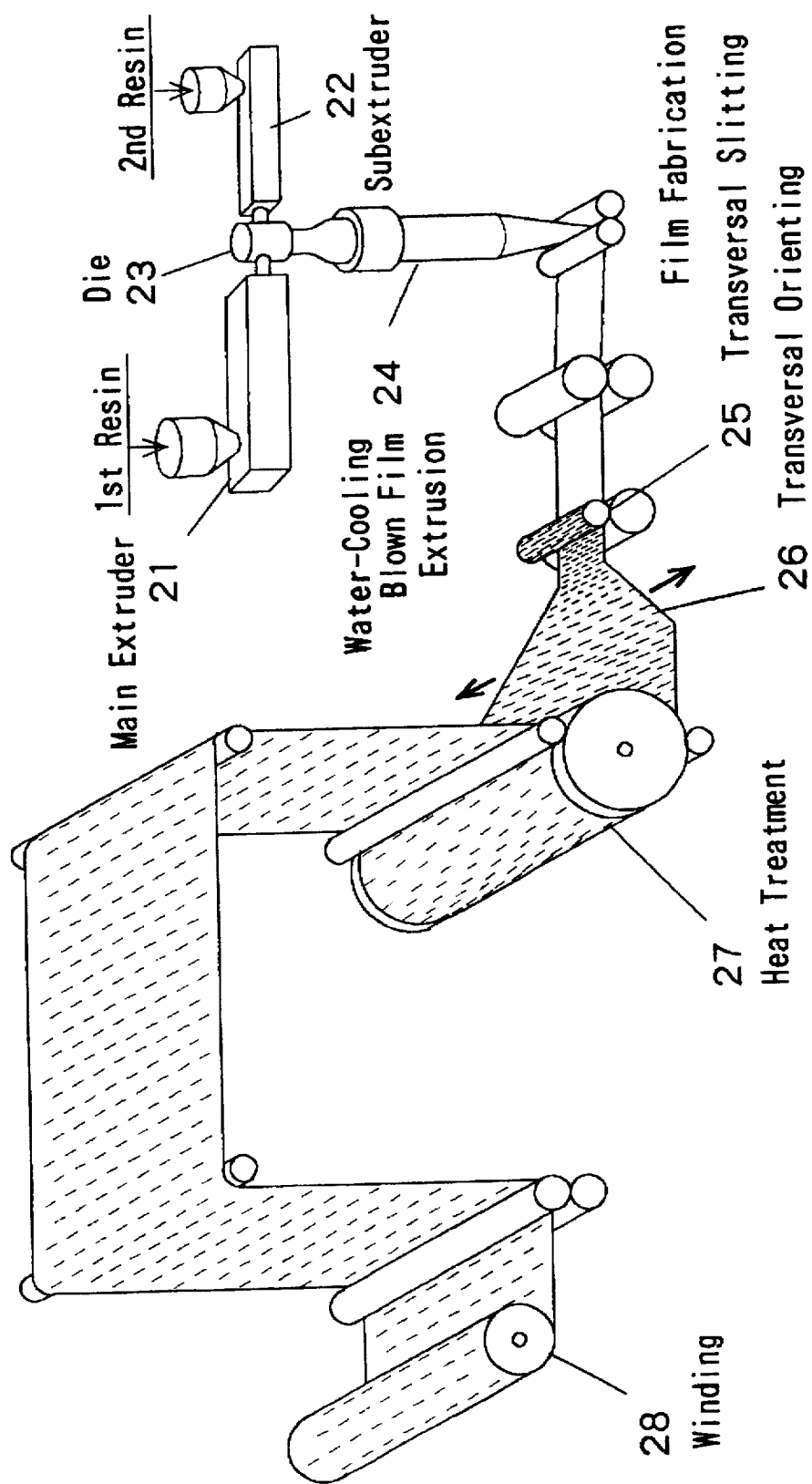

COMPOSITE MATERIAL WITH CONTROLLED ELASTICITY

BACKGROUND OF THE INVENTION (1) Field of the Invention

The present invention relates to a composite material with controlled elasticity. More particularly, the invention relates to a composite material which is made by forming a flexible elastomer layer or layers on a specific monoaxially oriented material so as to exhibit controlled elasticity. The composite materials of this kind with the controlled elasticity are widely used for producing disposable diapers, clothing, gloves, shoe covers, caps, adhesive plasters, bandages, and tapes for winding round joint tubes of electric wires and pipings.

(2) Description of the Prior Art

There has been proposed various kinds of sheet materials having flexibility, elasticity or resilience as those for producing sportswear for skiing, motor sports and marine sports, clothes for working and surgical operation, working gloves in food works, gathers of caps and hats, bracelets, suspenders, belts, poultices, diapers and so forth.

For example, the method for producing elastic composite material by combining an elastic and flexible material and a non-elastic material for forming pleats is disclosed in Japanese Laid-Open Patent Publication Nos. Sho 59-59901, Sho 62-33889, Hei 6-31833, Hei 6-31869, and Hei 6-47808. A method for producing embossed elastic fabric made of elastic fabric and non-elastic sheet is disclosed in Japanese Laid-Open Patent Publication No. Sho 63-92433. Methods for laminating non-woven fabric and rubber-like elastic threads are disclosed in Japanese Laid-Open Patent Publication Nos. Sho 61-289163 and Hei 3-213543. Methods for a laminating polyurethane film and polyurethane nonwoven fabric are disclosed in Japanese Laid-Open Patent Publication Nos. Sho 62-121045 and Sho 62-162538. A method for producing elastic laminates of specific thermoplastic rubber layers and non-woven fabric is disclosed in Japanese Laid-Open Patent Publication No. Hei 3-158236.

In the fixtures for the waist parts of disposable diapers, clothes for working and surgical operation, caps for food works, garbage collecting and IC manufacturing works, fixtures for gloves and shoe covers, adhesive plasters, and bandages, it is required that the materials exhibit controlled proper flexibility and elasticity in one direction or in various directions as well as mechanical strength. However, the elastic and flexible composite materials disclosed in the foregoing references can neither meet these requirements nor be produced easily at low cost.

BRIEF SUMMARY OF THE INVENTION

The present inventors have carried out intensive investigations to solve the above-mentioned problems.

As a result, it has been found out that an elastic composite material exhibiting mono-axially or multi-axially controlled proper flexibility and elasticity as well as mechanical strength can be produced by combining a specific monoaxially oriented material made of thermoplastic resin with an a flexible elastomer layer. In consequence, the present invention has been accomplished.

It is, therefore, a first object of the present invention to provide a controlled elastic composite material which is produced by forming a flexible elastomer layer or layers on one or both surfaces of at least one member selected from the group consisting of the following monoaxially oriented materials (a), (b), (c) and (d) which are made of thermoplastic resin:

(a) a longitudinally monoaxially oriented reticular web, (b) a transversally monoaxially oriented reticular web, (c) a woven or non-woven fabric composed of monoaxially oriented tapes, and (d) a stretched long fiber web in which long fibers, including continuous fibers, are aligned almost in one direction.

A second object of the present invention is to provide the controlled elastic composite material which is made by forming a flexible elastomer layer or layers on one or both surfaces of the composite material, which composite material is made by laminating crosswise at least one kind of above-mentioned monoaxially oriented materials of (a), (b), (c) and (d) at an angle of 10° to 80°.

In the present invention, because the controlled elastic composite material is made by forming a flexible elastomer layer or layers on one or both surfaces of the composite material, which composite material is made by laminating crosswise specific monoaxially oriented reticular web or stretched long fiber web at an angle of 10° to 80°, the product of elastic composite material exhibits proper controlled flexibility and elasticity in one axial direction or in both longitudinal and transversal directions. In addition, it has very high mechanical strength. Especially, when the stretched long fiber web is used, the product has large strength as well as excellent feeling and drape.

BRIEF DESCRIPTION OF THE DRAWINGS

These and other objects and features of the present invention will become more apparent in the following description with reference to several embodiments and accompanying drawings, in which:

FIG. 2 is a schematic illustration of a process for producing the longitudinally monoaxially oriented reticular web (a) of the present invention, FIG. 4 is a schematic illustration of a process for producing the transversally monoaxially oriented reticular web (b)

DETAILED DESCRIPTION OF THE INVENTION

The present invention will be described in more detail.

Figure 1A:
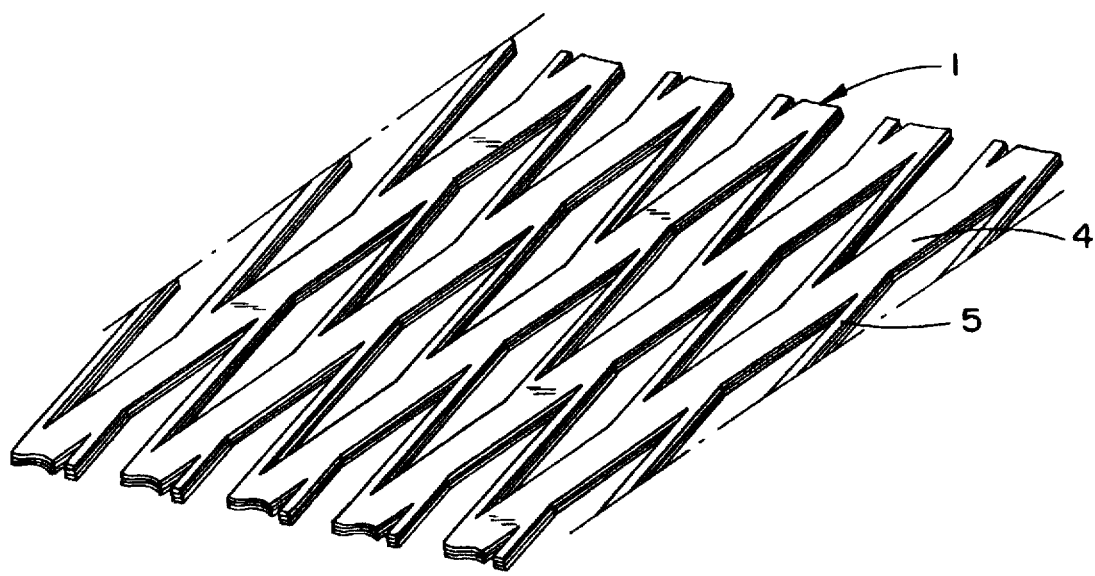
FIG. 1A is an enlarged perspective view of a part of a longitudinally monoaxially oriented reticular web (a)

FIG. 1A is an enlarged perspective view of a longitudinally monoaxially oriented reticular web (a).

Figure 1B:
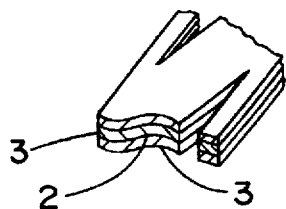
FIG. 1B is a schematic illustration of the laminate layers of a longitudinally monoaxially oriented reticular web (a)

The longitudinally monoaxially oriented reticular web 1 shown in FIG. 1A is prepared by laminating second thermoplastic resin layers 3 to both the surfaces of a first thermoplastic resin layer 2 to obtain a multi-layer film, as depicted in FIG. 1B, and it is subjected to orientation treatment of stretching and/or rolling. The oriented film is then treated in a fibrillation process in which it is subjected to cross-stitch pattern splitting in the longitudinal direction. In this drawing, the reticular web 1 consists of stem fibers 4 and branch fibers 5.

As shown in FIG. 2, the longitudinally monoaxially oriented reticular web (a) is prepared through the steps of:

(1) a film fabrication step for preparing a multi-layer film, (2) an orientation step for orienting the multi-layer film, (3) a fibrillation step for splitting the oriented multi-layer film in a direction parallel to the orientation axis, and (4) a winding step for winding the fibrillated film.

The each of the above steps will be described in more detail.

In the film fabricating step for producing the multi-layer film of the present invention in FIG. 2, a first thermoplastic resin is fed to a main extruder 11 and a second thermoplastic resin is fed to two subextruders 12, 12, respectively. The multi-layer film is then formed, in which the film comprises an inner core layer (an orienting layer) made of the first thermoplastic resin fed from the main extruder 11 and outer layers of the second thermoplastic resin fed from the two subextruders 12, 12. In the present invention, the film is fabricated through a multi-layer circular die 13 with the three extruders and through the water-cooling down-blow extrusion process 14. However, the method for preparing the multi-layer film is not limited to the multi-layer blown film extrusion method or the multi-layer T-die method. In various methods, the water-cooling blown film extrusion method is preferable because it has an advantage that a rather thick film can be cooled rapidly without losing the transparency of the film.

In the orientation step of the present invention, the tubular multi-layer film prepared in the above step is flattened and cut into two sheets of films F, F', and these films are then oriented at an orientation ratio of 1.1 to 15, preferably 5 to 12, more preferably 6 to 10, relative to the initial size. In the orientation step, the two sheets of films are heated to a predetermined temperature by an oven 15 which is equipped with infrared heaters or hot-air fans.

The above-mentioned orientation temperature is lower than the melting point of the first thermoplastic resin of the core layer, and it is usually in the range of 20° to 160° C., preferably 60° to 150° C., and more preferably 90° to 140° C. The orientation is preferably carried out step by step in a multi-stage apparatus.

For carrying out the orientation, there are a roll stretching method (free monoaxially stretching method), hot plate stretching method, cylinder stretching method, hot air stretching method and rolling method. The orientation method as referred to in the present invention includes these ordinary stretching method as well as the rolling method. Any one of the above-mentioned orientation methods can be used, however, the rolling method, especially the free monoaxially stretching method is preferable.

The rolling method referred to in the present invention is a method in which a thermoplastic resin film is passed between a set of two hot rolls having a gap smaller than the thickness of the film, and the film is pressed through the gap at a temperature lower than the melting point (softening point) of the resin film, thereby stretching the film as much as the ratio of decrease in thickness.

The free monoaxially stretching method as herein referred to means a method in which the stretching distance (the distance between a low-speed roll and a high-speed roll) is made sufficiently larger than the width of the film, and the film is stretched freely with allowing the decrease of the width of film.

In the fibrillation step of the present invention, the multi-layer film which has been oriented in the above step is brought into sliding contact with a fibrillator (rotary blades) 16 which is rotated at a high speed so as to fibrillate the films F, F'.

As the above-mentioned fibrillation method, there can be used any one of methods to make numerous cuts or slits in the monoaxially oriented multi-layer film such as mechanical methods to beat, twist, scrape, rub, or brush the monoaxially oriented films or other methods using air jet, ultrasonic wave or laser beams.

Among these fibrillation methods, the rotary mechanical method is preferable. In the rotary mechanical method, fibrillators of various types such as a tapping screw type splitter, a file-like coarse surface splitter and a needle roll splitter can be used. For example, a preferable tapping screw type splitter is usually in the shape of pentagonal prism or a hexagonal prism and 10 to 40 threads, preferably 15 to 35 threads per inch. The preferable file-like coarse surface splitter is disclosed in Japanese Utility Model Publication No. Sho 51-38980. The file-like coarse surface splitter is a rod whose cross-section is circular and has a surface like a round file for iron works or a similar ones. On the surface of the rod, two spiral grooves are formed at a regular pitch. Typical examples of such file-like coarse surface splitter are also disclosed in U.S. Pat. Nos. 3,662,935 and 3,693,851.

The method for making the above-mentioned reticular web is not limited particularly. However, a preferable method comprises arranging a splitter between nip rolls, moving the monoaxially oriented multi-layer film along the splitter under tension, and bringing the film into sliding contact with the splitter which is rotated at a high speed, so as to fibrillate the film into a reticular film.

The moving velocity of the film is usually in the range of 1 to 1000 m/min, preferably 10 to 500 m/min. Furthermore, the rotational speed (peripheral velocity) of the splitter can be suitably selected in consideration of the physical properties and the moving velocity of the film, and the desired properties of the reticular film to be obtained. The rotational speed is usually in the range of 10 to 3000 m/min, and preferably 50 to 1000 m/min.

The longitudinally monoaxially oriented reticular web (a) which has been thus fibrillated by splitting is, if desired, spread in the direction of its width, subjected to a heat roll 17 in the heat treatment step, wound up to a predetermined length on a winding roll 18 in the winding step, and the obtained roll is supplied as a final product.

The transversally oriented reticular web (b) according to the present invention can be a single-layer film, however, it is preferably the one which is formed by the lamination of a second thermoplastic resin film or films on one or both surfaces of a first thermoplastic film, in which the melting point of the second thermoplastic film is lower than that of the first thermoplastic film. The laminated multi-layer film is then fibrillated in parallel to the direction to be oriented (transversal) using a slitter or other fibrillating device in a cross-stitch pattern, which is followed by transversal stretching or rolling, heat treatment and width spreading.

Figure 3B:
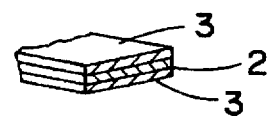
FIG. 3B is a schematic illustration of the laminate layers of a transversely monoaxially oriented reticular web (b)
Figure 3A:
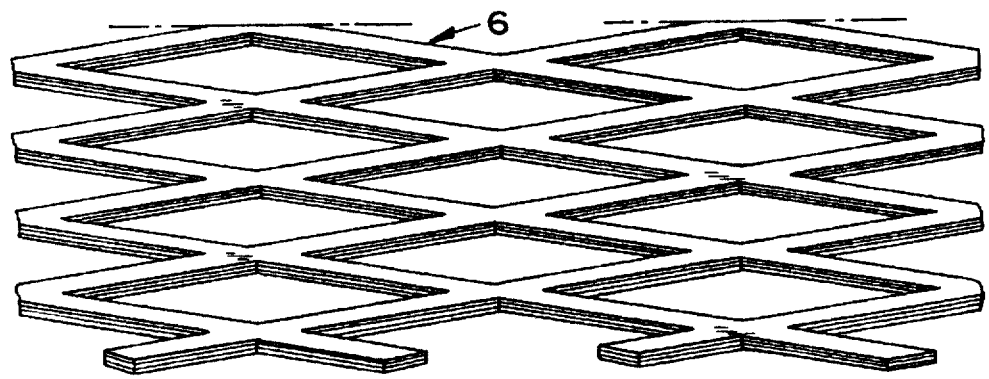
FIG. 3A is an enlarged perspective view of a part of a transversally monoaxially oriented reticular web (b)

FIG. 3A shows an enlarged partial perspective view of a transversally monoaxially oriented reticular web (b) of an embodiment of the present invention.

FIG. 3B illustrates the transversally monoaxially oriented reticular web 6 to be a multi-layer film which is composed of a first thermoplastic resin layer 2 and second thermoplastic resin layers 3 which are applied to both surfaces of the first thermoplastic resin layer 2.

FIG. 4 is a schematic illustration of an embodiment of the manufacturing process for producing the transversally monoaxially oriented reticular film (b) in accordance with the present invention.

The transversally monoaxially oriented reticular web b is made through the steps of:

(1) a film fabrication step for preparing a multi-layer film, (2) a slitting step for fibrillating the multi-layer film, (3) an orienting step for stretching the multi-layer film in the direction parallel to the direction of slitting, and (4) a winding step for winding the slit and oriented film.

The respective steps will be described.

In FIG. 4, in the film fabrication step for preparing the multi-layer film, a first thermoplastic resin is fed to a main extruder 21 and a second thermoplastic resin is fed to a subextruder 22. The blown film extrusion is then carried out to form a tubular film. This tubular film is composed of two layers of an inner layer of the first thermoplastic resin from the main extruder 21 and an outer layer of the second thermoplastic resin from the subextruder 22. In the present invention, the film can be formed through a multi-layer circular die 23 with the use of the two extruders through down-blow water-cooling blown film extrusion 24. The method for preparing the multi-layer film is not particularly limited to this multi-layer blown film extrusion method or a multi-layer T-die film method as stated in the description on the longitudinally monoaxially oriented reticular film (a). Among these film forming methods, the water-cooling blown film extrusion method is preferable because the method has an advantage that a transparent film can be produced by rapidly cooling a thick film. In addition, according to the present invention, the obtained film is slightly oriented by pressing it between rolls so as to bond the inner layers of the flattened tube, thereby obtaining a three-layer film composed of the layers of [second thermoplastic resin/first thermoplastic resin/second thermoplastic resin]. In this method, the two extruders are used in place of the three extruders for preparing the foregoing longitudinally monoaxially oriented reticular web, which method leads to a large economical advantages.

In the slitting step of the present invention, the tubular multi-layer film is flattened by pinching, slightly oriented by rolling into the a three-layer film of [second thermoplastic resin/first thermoplastic resin/second thermoplastic resin]. In the transversally slitting step 25, the film is then transversally slit at right angles to its running direction (TD) to form numerous slits in cross-stitch pattern in the film. The above-mentioned slitting is attained by using sharp blades such as razor blades or high-speed rotary cutting blades, a score cutter, a shear cutter or a heat cutter. Among them, the slitting with the heat cutter is most preferable.

Some examples of the heat cutter are disclosed in Japanese Patent Publication No. Sho 61-11757, U.S. Pat. No. 4,489,630, and U.S. Pat. No. 2,728,950. The slitting with a heat cutter produces an effect that the edges of slits in the slightly oriented film by the rolling in the previous step, are rounded and thickened by partial fusion. Owing to this effect, the slits can be prevented from tearing and over running of slits in the succeeding transversally orienting step.

In the orienting step of the present invention, the slit film is transversally (TD) oriented in the section 26. The orientation can be carried out by a tenter method or a pulley method, in which the pulley method is preferable because a small-sized device can be used economically. This pulley method is disclosed in British Patent No. 849436 and Japanese Patent Publication No. Sho 57-30368. The conditions for the orienting are the same as those in the above-mentioned orientation step for the longitudinally monoaxially oriented reticular web.

The transversally monoaxially oriented reticular web (b) is then subjected to heat treatment 27 and wound in the winding step 28.

The above-mentioned monoaxially oriented multi-layer tape (c) for the woven fabric or non-woven fabric is produced by monoaxially orienting a multi-layer film of the first thermoplastic resin layer and second thermoplastic resin layer which is prepared by a multi-layer extrusion such as blown film extrusion or multi-layer T-die film method. The multi-layer film is monoaxially oriented at a orienting ratio of 1.1 to 15, preferably 3 to 10 before and/or after the cutting. The cut tapes are formed into woven fabric or non-woven fabric by putting them together crosswise at an angle of 10° to 80°. In some case, it is possible that the monoaxially oriented tapes are aligned in parallel and temporarily stuck together and they are laminated crosswise with an elastomer sheet or sandwiches with elastomer sheets to obtain the elastic composite material of the present invention.

Figure 5:
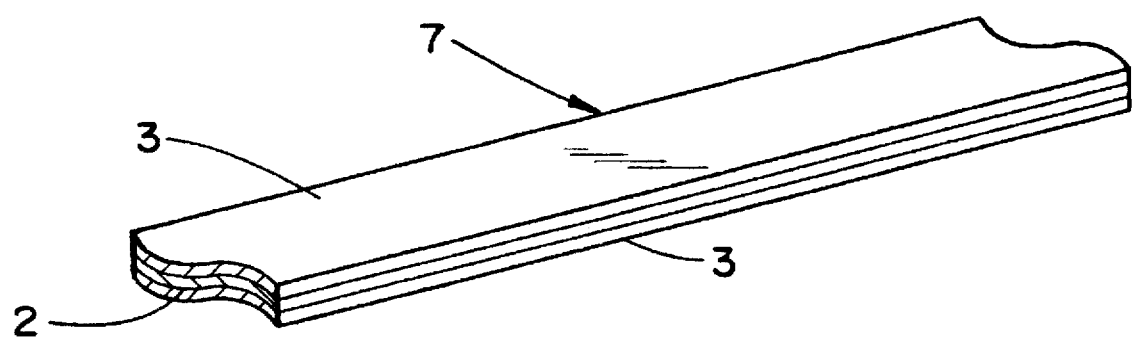
FIG. 5 is an enlarged perspective view of a monoaxially oriented tape (c) of an embodiment of the present invention.

FIG. 5 is an enlarged perspective view of an embodiment of a monoaxially oriented multi-layer tape (c). In this drawing, a monoaxially oriented multi-layer tape 7 comprises a first thermoplastic resin layer 2 and second thermoplastic resin layers 3, 3.

The ratio of thicknesses of the first thermoplastic resin layer and the second thermoplastic resin layer is not especially limited. It is, however, preferable that the thickness of the second thermoplastic resin layer is not more than 50% to the total thickness, preferably less than 40% in order to maintain the mechanical strength of the multi-layer tape. The thickness of the multi-layer film or the first thermoplastic resin layer after the orienting is preferably about 20 to 100 μm. The thickness of the second thermoplastic resin layer is 3 μm or more in view of several properties such as the adhesive strength in thermal adhesion. The thickness is, however, generally in the range of 3 to 60 μm, preferably 5 to 40 μm.

Examples of the foregoing first thermoplastic resins are homopolymers of α-olefins such as high density and medium density polyethylenes, polypropylene, polybutene-1, poly-4-methylpentene-1, and polyhexene-1; copolymers of α-olefins such as ethylene-propylene copolymer; and other polymers of polyamide, polyester, liquid-crystalline polyester, polycarbonate and polyvinyl alcohol. So long as it is a crystalline resin which excels in stretching property, the resin is not especially limited.

Examples of the foregoing second thermoplastic resins which have melting points lower than that of the first thermoplastic resin are non-polar polyethylenes such as high density, medium density and low density polyethylenes, linear low density polyethylene, and ultra low density polyethylene; ethylene-vinyl ester copolymers such as ethylene-vinyl acetate copolymer; ethylene-acrylic ester copolymer such as ethylene-ethylacrylate copolymer; ethylene-methacrylic ester copolymer such as ethylene-ethylmethacrylate copolymer; copolymers of ethylene and α, β-unsaturated carboxylic acid such as the copolymer of ethylene and maleic acid or its ester; propylene polymers such as polypropylene and ethylene-propylene copolymer; modified-polyolefin which is modified with unsaturated carboxylic acid; and mixture of the above materials.

It is desirable that the difference of melting points of the above first thermoplastic resin and the second thermoplastic resin is not lower than 5° C. in order to facilitate the production with maintaining the orienting characteristics of the first thermoplastic resin and crosswise lamination of monoaxially oriented materials. More preferable temperature difference is 10° to 50° C.

The stretched long fiber web (d) of the present invention is made by spinning long fibers with a thermoplastic resin, monoaxially stretching the web so as to align the long fibers in one direction. The ratio of stretching of the long fiber web is in the range of 5 to 20 and the average degree of fineness of the fiber is in the range of 0.01 to 10 denier.

The stretched long fiber web (d) of the present invention is composed of stretched long fibers most of which fibers are regularly aligned in one direction in the plane of the web. More particularly, the following long fiber webs are prepared:

(1) A long fiber web which is made by spinning a thermoplastic resin into continuous fibers and by hot air circularly moving or by vibration. The web is composed of spun filaments which can be stretched in the stretching ratio of 2 or higher.

(2) A long fiber web which is made by spinning a thermoplastic resin and by stretching, untangling, accumulating and sheet formation.

(3) A long fiber web which is made by subjecting the bundles of long fibers of a thermoplastic resin to stretching, crimping, untangling, and width spreading.

(4) A web which is made by expanding flashingly of a thermoplastic resin with the special solvent and accumulating and sheet formation.

(5) A melt blown non-woven fabric which is formed by spraying a thermoplastic resin together with high pressure and high temperature, and then by untangling and aligning.

The long fiber web is then stretched longitudinally and/or transversally by rolling, near-roll stretching, tenter stretching, pulley stretching or hot plate stretching, and if necessary, it is further subjected to aligning treatment roughly in one direction to obtain the stretched long fiber web (d) of the present invention.

Figure 6:
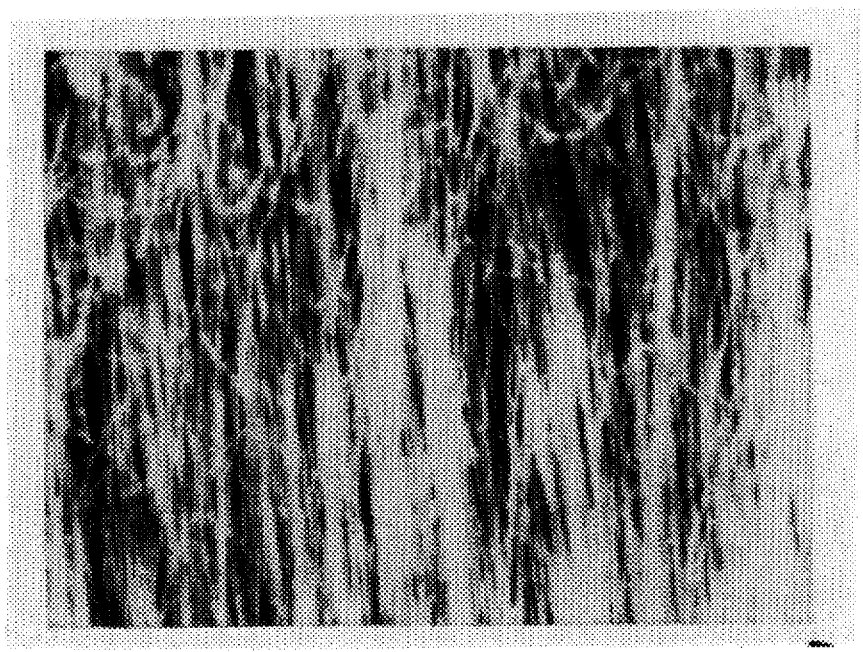
FIG. 6 is a microphotograph of the stretched long fiber web (d)

FIG. 6 is a microphotograph (magnification: 17) of the stretched long fiber web (d) in which stretched long fibers are aligned almost in one direction.

Particular methods for producing the above stretched long fiber web (d) are disclosed in Japanese Patent Publication No. Hei 3-36948 and Japanese Laid-Open Patent Publication Nos. Hei 2-242960 and Hei 2-269859.

Figure 7:
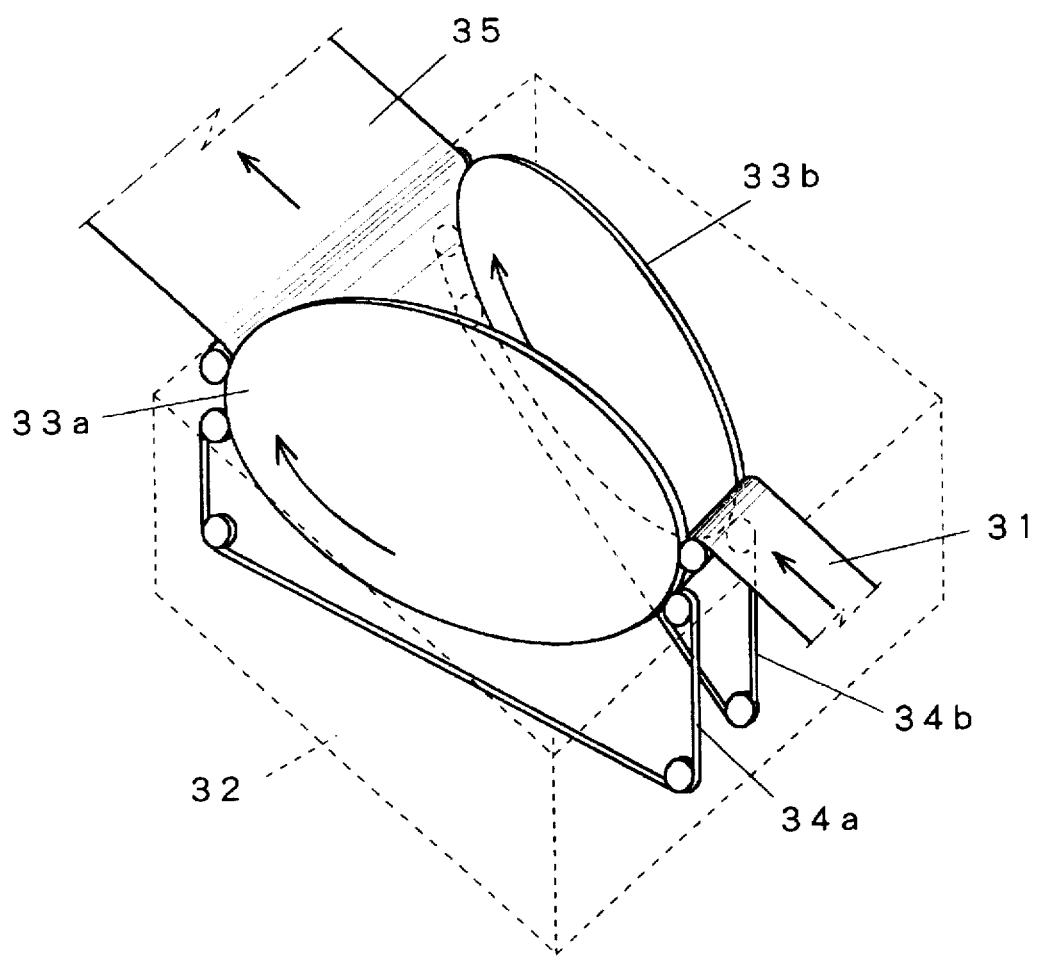
FIG. 7 is schematic partial perspective view of a transversally stretching device.

In one example, melting filaments which are extruded from apertures of spinning head are scattered by circularly moving air and they are accumulated on a conveyor belt to obtain a long fiber random non-woven fabric having longitudinal or transversal alignment of fibers. Using the transversally stretching device as shown in FIG. 7, a long fiber web in which fibers are previously aligned transversally is transversally stretched under hot air blowing.

The transversally aligned web is stretched in the direction of transverse with a transversally stretching device. An example of the transversally stretching device is shown in FIG. 7, in which a web 31 composed of transversally aligned long fibers is introduced into a heating chamber 32 and it is stretched by the pulley-type transversally stretching device.

In this device, both the selvages of web 31 are pinched with a pair or stretching pulleys 33a, 33b and circulating belts 34a, 34b which run along the circumference of the pulleys 33a, 33b. Because the distance between the pulleys are enlarged in the downstream side, the web 31 is stretched transversally.

It is possible to control the ratio of stretching by changing the angle of opening between both the pulleys, however, if the ratio of stretching is very large, the stretching may be done in multi-stage treatment.

As the heating medium in the heating chamber 32, hot water, hot air or steam may be used.

Figure 8:
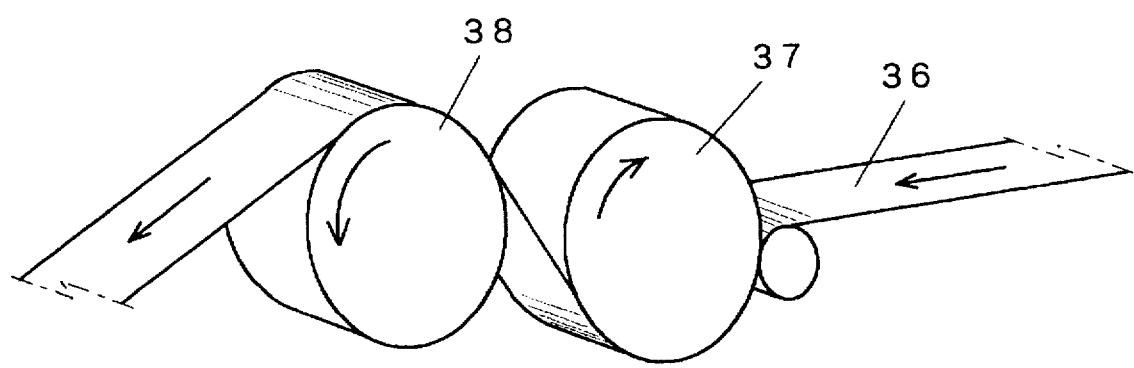
FIG. 8 is schematic partial perspective view of a near-roll stretching device.

FIG. 8 is a schematic partial perspective view of a near-roll stretching device. A long fiber web 36 in which fibers are previously aligned in longitudinal direction is passed around the rolls 37, 38, the rotational speeds of which rolls are different from each other. The rotational speed of the upstream roll 37 is smaller than that of the downstream roll 38, thereby attaining the stretching of the web 36 without excessively reducing the width of web 36. In the present invention, the combination of the above devices can also be employed.

The ratio of stretching of the above stretched long fiber web is in the range of 5 to 20, preferably 8 to 12. The average degree of fineness of the long fiber is in the range of 0.01 to 10 denier, preferably 0.01 to 5 denier. More particularly, the 0.01 to 10 denier fibers which are made by rolling or stretching spun filaments of 0.2 to 50 denier, are desirable.

The unit weight of the above long fiber web is selected from the range of 5 to 100 g/m$^2$, which differs in view of uses and purposes.

A stretched long fiber web according to the present invention is preferably a conjugated fiber material which is made of a first thermoplastic resin having a relatively higher melting point and a second thermoplastic resin having a melting point lower than that of the first thermoplastic resin. The conjugated fiber is exemplified by a long fiber which is composed of a core material made of the first thermoplastic resin having a higher melting point and a sheath material of the second thermoplastic resin having a lower melting point; a long fiber web in side-by-side structure in which first thermoplastic resin fibers and second thermoplastic resin fibers are aligned in parallel; and a mixed long fiber web in which first thermoplastic resin fibers and second thermoplastic resin fibers are mixed together.

Examples of thermoplastic resins used for producing the above-mentioned long fiber web may be the same as those used for producing the foregoing monoaxially oriented reticular web such as polyolefin resins including polyethylene and polypropylene, polyester resins, polyamide resins, and polyvinyl alcohol resins.

The composite material used in the second aspect of the invention is the one which is made by laminating crosswise at least one of the monoaxially oriented materials of (a), (b), (c) and (d) at an angle of 10° to 80°. In other words, in the composite material, the angle between the direction of orientation and the direction of warp or weft is in the range of 10° to 80°. In addition, it is desirable that the angle between the direction of forming of the flexible elastomer layer and the direction of warp or weft is also 10° to 80°. More particularly, the lamination is done in such a manner that, if the angle between the direction of elastomer formation and the direction of warp is 10° to 80° clockwise, the angle between the direction of elastomer formation and the direction of weft is 10° to 80° counterclockwise.

In the lamination of the monoaxially oriented reticular web of (a), (b) and (c) or the monoaxially oriented tapes are laminated, the thermal adhesion must be done at a temperature above the melting point of the second thermoplastic resin but within the range that the lowering of elasticity of the first thermoplastic resin can be avoided.

In the case of stretched long fiber web (d), it is desirable that the lamination is carried out by using the foregoing conjugated fibers having the sheath structure or the combined long fiber web composed of the long fibers of first thermoplastic resin of higher melting point and the long fibers of second thermoplastic resin of lower melting point. These fibers may be adhered together with known adhesives of polyurethane, vinyl acetate copolymer or else.

The flexible elastomers used in the present invention include thermoplastic elastomers, synthetic rubber and natural rubber.

The above thermoplastic elastomers are exemplified by polyolefins (TPO), polyamides, polystyrenes, polyvinyl chlorides, polyesters, and polyesters. Among them, thermoplastic polyurethane elastomers are preferable because of their excellent overall properties in elasticity, durability and economy.

The above thermoplastic polyurethane elastomers are exemplified by the polymers which are made by reacting organic diisocyanates such as tolylenediisocyanate and p,p'-diphenylmethane diisocyanate with low melting point polyols such as dihydroxy polyether and dihydroxy polyester in the presence of a chain propagating agent.

The above synthetic rubbers are exemplified by polyurethane rubber, ethylene-propylene rubber, nitrile rubber and isobutylene rubber.

The above ethylene-propylene rubber includes the random copolymer of main components of ethylene and propylene (EPM) and the random copolymer (EDPM) which is made by adding a third component of diene monomer such as dicyclopentadiene or ethylydenenorbornene to the above EPDM.

In the case that the flexible elastomer layers used in the present invention are prepared in advance, it is possible to employ various methods such as blow film method, T-die method or calender method with extrusion, fluidized dip coating method, and casting method with a polyurethane solution for producing films or sheets, or spun bonded method and melt blown method for producing non-woven fabric.

The methods for forming the flexible elastomer on one surface or both surfaces of the specific monoaxially oriented material in the present invention are exemplified by extrusion lamination, chemical sheeting and thermal bonding.

In the case that polyurethane film prepared by a polyurethane solution casting method is used, the obtained cast film is applied with an adhesive agent, preferably an adhesive agent of low polymerization degree urethane, and it is laminated with a monoaxially oriented material. After that, the urethane adhesive agent is cured under heat and pressure to obtain the elastic composite material of the present invention.

It is desirable that the surface of monoaxially oriented material is treated in the preparation of the elastic composite material of the present invention, in order to enhance the adhesive strength. The surface treatment includes well known physical surface treatment methods such as corona discharge treatment, plasma treatment, and UV radiation treatment and chemical surface treatment method such as solvent treatment. Among them, the corona discharge treatment is advantageous in view of its effect and cost. The wetting index of the surface of the above surface-treated material is 40 dyne/cm or higher, preferably above 42 dyne/cm, and more preferably above 45 dyne/cm.

The elastic composite material of the present invention may be composed of a monoaxially oriented web and flexible elastomer layer or layers. These materials can be used in combination with other suitable materials. For example, provided that the monoaxially oriented material is B and the flexible elastomer layer is B and other material is X, A, the following combinations of materials are exemplified: A/B, A/B/X, A/X/B and X/A/B.

The above other materials includes spun bonded non-woven fabric and melt blown non-woven fabric made of various resins such as polyethylene terephthalate (PET), polypropylene (PP), and polyamide (PA); dry-type or wet-type non-woven fabrics made of artificial fibers such as PET, PA and rayon, and natural fibers such as cotton and wool; and other sheet materials such as cloth, paper, rubber film and leather.

In the present invention, various known additives can be added to the above monoaxially oriented material and the flexible elastomer layer so long as the characteristic features of the invention are not impaired. Such additives are exemplified by antistatic agents, anti-fogging agents, organic or inorganic fillers, anti-oxidizing agents, lubricants, organic or inorganic pigments, UV ray absorbers, dispersing agents, nucleating agents, foaming agents, flame retardants, and cross-linking agents.

The present invention will be described in more detail with reference to examples. It is to be noted, however, that the scope of the present invention should not be limited to these examples.

EXAMPLE 1

In the process as shown in FIG. 2, a longitudinally monoaxially oriented reticular web (a) was prepared through the following procedure.

In a film fabrication step, a multi-layer film of triple-layer structure having a thickness ratio of [adhesive layer 15 μm/core layer 100 μm/adhesive layer 15 μm] and width of 1 m was prepared through multi-layer water cooling blown film extrusion method. The first thermoplastic resin (core layer) was made of high-density polyethylene (density= 0.956 g/cm$^3$, MFR=1.0 g/10 min, trademark: Nisseki Staflene E 710, made by Nippon Petrochemicals Co., Ltd.) and the second thermoplastic resin laminated as adhesive layers on both surfaces of the core layer was made of low-density polyethylene (density=0.924 g/cm$^3$, MFR=3.0 g/10 min, trademark: Nisseki Rexlon F30, made by Nippon Petrochemicals Co., Ltd.).

In the next orientation step, it was monoaxially stretched at a stretching ratio of 9 to form a monoaxially stretched film of 40 μm in thickness and 30 cm in width. The stretched film was then treated with a splitting device as disclosed in Japanese Utility Model Publication No. Sho 51-38979 to form numerous splits in the film forming direction (MD), thereby preparing a longitudinally monoaxially oriented reticular web (a) of 10 g/m$^2$ in unit weight, 11 kg/5 cm in tensile strength and 20% in elongation.

In the next step, both surfaces of the longitudinally monoaxially oriented reticular web (a) were subjected to corona discharge treatment to make the wet tension of the surfaces 45 dyne/cm. Polyurethane thermoplastic elastomer films of 20 μm in thickness were laminated with the web (a) using an adhesive agent, thereby preparing a controlled elastic composite material having monoaxial elasticity.

The stress at 100% elongation of the obtained monoaxially elastic composite material was 100 g/cm.

EXAMPLE 2

Both surfaces of the longitudinally monoaxially oriented reticular web (a) obtained in Example 1 were likewise applied with films of ethylene-propylene random copolymer rubber film of 20 μm in thickness using an adhesive agent to obtain a monoaxially elastic composite material.

The stress at 100% elongation of the obtained monoaxially elastic composite material was 160 g/cm.

EXAMPLE 3

Both surfaces of the longitudinally monoaxially oriented reticular web (a) obtained in Example 1 were applied likewise with polyurethane spun bonded non-woven fabric of 25 g/m² in unit weight and 0.12 mm in thickness (trademark: Espunsione UH 025, made by Kanebo, Ltd.) using an adhesive agent to obtain a monoaxially elastic composite material.

The stress at 100% elongation of the obtained monoaxially elastic composite material was 80 g/cm and the recovery ratio after 100% elongation was 90%.

EXAMPLE 4

Both surfaces of the longitudinally monoaxially oriented reticular web (a) obtained in Example 1 were applied likewise with polyurethane melt blown non-woven fabric of 20 g/m² in unit weight and 0.10 mm in thickness using an adhesive agent to obtain a monoaxially elastic composite material.

The stress at 100% elongation of the obtained monoaxially elastic composite material was 60 g/cm and the recovery ratio after 100% elongation was 85%.

EXAMPLE 5

In a film fabrication step, a multi-layer film of triple-layer structure having a thickness ratio of [adhesive layer 15 μm/core layer 100 μm/adhesive layer 15 μm] and width of 90 cm was prepared through multi-layer water cooling blown film extrusion method. The first thermoplastic resin (core layer) was high-density polyethylene (density=0.956 g/cm³, MFR=1.0 g/10 min, trademark: Nisseki Staflene E 710, made by Nippon Petrochemicals Co., Ltd.) and the second thermoplastic resin laminated as adhesive layers on both surfaces of the core layer was low-density polyethylene (density=0.924 g/cm³, MFR=3.0 g/10 min, trademark: Nisseki Rexlon F 30, made by Nippon Petrochemicals Co., Ltd.).

In the next orientation step, multi-layer film was monoaxially stretched at a stretching ratio of 9 to prepare a monoaxially stretched film of 40 μm in thickness and 30 cm in width. The stretched film was then treated with a splitting device as disclosed in Japanese Utility Model Publication No. Sho 51-38979 to form numerous splits in the longitudinal direction (MD), and the width of the obtained split film was spread three times transversally, thereby preparing a longitudinally monoaxially oriented reticular film (a). A pair of the obtained reticular films were laminated crosswise at an angle of 60° of orientation axes to prepare a composite material A.

In the next step, both surfaces of the composite material A were subjected to corona discharge treatment and polyurethane thermoplastic elastomer of 20 μm in thickness was formed by extrusion lamination method on both surfaces of the composite material A. In the extrusion lamination, the direction of warp of the composite material A was inclined by 30° clockwise to the direction of elastomer formation and the direction of weft of the composite material A was inclined by 30° counterclockwise to the direction of elastomer formation to obtain a elastic composite material.

The ratio of elongation of the obtained elastic composite material in MD was 15% and in TD, 50%.

EXAMPLE 6

A multi-layer film was prepared in the like manner as in the process in FIG. 4 and the multi-layer film was stretched transversally (TD) in the orientation step to obtain a transversally monoaxially oriented reticular web (b). This web (b) was crosswise laminated with the longitudinally monoaxially oriented reticular web (a) such that the axes of orientation of both the webs intersected at an angle of 60° to obtain a composite material B.

In the next step, both surfaces of the composite material B were applied with 20 μm thick polyurethane thermoplastic elastomer by extrusion lamination method in the like manner as in Example 5. In the extrusion lamination, the direction of warp of the composite material B was inclined by 60° clockwise to the direction of the formation of elastomer and the direction of weft of the composite material A was inclined by 60° counterclockwise to the direction of elastomer formation to obtain a elastic composite material.

The ratio of elongation of the obtained elastic composite material in MD was 50% and in TD, 15%.

EXAMPLE 7

Experiment was carried out in the like manner as in Example 5 except that the longitudinally monoaxially stretched film was cut into monoaxially oriented tapes (c) and two groups of the tapes were laminated crosswise with an intersecting angle of orientation axes of 60° to obtain a monoaxially oriented non-woven fabric.

The ratio of elongation of the obtained elastic composite material in MD was 15% and in TD, 50%.

EXAMPLE 8

Experiment was carried out in the like manner as in Example 5 except that the longitudinally monoaxially stretched film was cut into monoaxially oriented tapes (c) and two groups of the tapes were woven crosswise with an intersecting angle of orientation axes of 60° to obtain a monoaxially oriented woven fabric.

The ratio of elongation of the obtained elastic composite material in MD was 15% and in TD, 50%.

In the following, the use examples of the stretched long fiber web (d) of the present invention are shown.

Evaluation of properties were done in accordance with the following methods:

(1) Tensile Strength

Tested according to JIS L 1096 and test pieces of 1 cm in width were used.

(2) Drape Property

Tested according to JIS L 1086, cantilever method.

Five (5) test pieces of 15 cm in length and 2 cm in width were prepared from stretched long fiber web, in which the direction of fibers are aligned with the long sides of test pieces. The scale was read when a test piece came into contact with the inclined plane of cantilever. If the obtained value was small, the test piece was regarded as flexible and good in drape property.

(3) Feeling

According to the following standard, the samples for feeling test was evaluated by 5 monitors who were voluntarily selected.

⊕: Determined as good by 4 or more monitors
O: Determined as good by 3 monitors
×: Determined as good by 2 or less monitors

EXAMPLE 9

In the first place, a stretched long fiber web was prepared according to the process disclosed in Japanese Patent Publication No. Hei 3-36948.

Filaments were prepared by spinning polypropylene (trademark: Nisseki Polypro J 120, made by Nippon Petrochemicals Co., Ltd.) and the obtained filaments were aligned transversally on a running conveyor belt with hot circularly moving air to obtain a long fiber web of spun filaments of 2 denier in fineness. With pulley-type transversally stretching method as disclosed in Japanese Laid-Open Patent Publication No. Sho 57-41922, the long fiber web was stretched by 10 times in transversal direction so as to make the fineness 0.2 denier and transversally stretched long fiber web of 8 g/m² in unit weight was prepared by means of temporary adhesion with polyvinyl alcohol.

In the next step, both surfaces of the stretched long fiber web were subjected to corona discharge treatment and polyurethane thermoplastic elastomer films of 20 μm in thickness were applied to the surfaces using an adhesive to obtain a monoaxially controlled elastic composite material.

The stress at 100% longitudinal elongation of the obtained elastic composite material was 100 g/cm and the maximum stress in transversal direction was 1000 g/cm, at which the maximum elongation was 7%. These results are shown in the following Table 1 together with the test results of drape property and feeling.

EXAMPLE 10

Both surfaces of the transversally stretched long fiber web obtained in Example 9 were subjected to corona discharge treatment and films of ethylene-propylene random copolymer rubber of 20 μm in thickness were laminated with an adhesive to obtain a monoaxially controlled elastic composite material.

The stress at 100% longitudinal elongation of the obtained composite material was 160 g/cm and the maximum stress in transversal direction was 1000 g/cm, at which the maximum elongation was 7%. These results are shown in the following Table 1.

EXAMPLE 11

Both surfaces of the transversally stretched long fiber web obtained in Example 9 were subjected to corona discharge treatment and polyurethane spun bonded non-woven fabric (trademark: Espunsione UH 025, made by Kanebo, Ltd.) of 25 g/m² in unit weight and 0.12 mm in thickness was laminated with an adhesive to obtain a monoaxially controlled composite material.

The stress at 100% longitudinal elongation of the obtained composite material was 80 g/cm and the maximum stress in transversal direction was 1000 g/cm, at which the maximum elongation was 7%. These results are shown in the following Table 1.

EXAMPLE 12

Both surfaces of the transversally stretched long fiber web obtained in Example 9 were subjected to corona discharge treatment and polyurethane melt blown non-woven fabric of 20 g/m² in unit weight and 0.10 mm in thickness was laminated with an adhesive to obtain a monoaxially controlled composite material.

The stress at 100% longitudinal elongation of the obtained composite material was 60 g/cm and the maximum stress in transversal direction was 1000 g/cm, at which the maximum elongation was 7%. These results are shown in the following Table 1.

COMPARATIVE EXAMPLE 1

The polyurethane spun bonded non-woven fabric (trademark: Espunsione UH 025, made by Kanebo, Ltd.) of 25 g/m² in unit weight and 0.12 mm in thickness as used in Example 11 was subjected to the similar measurement as above.

The stress at 100% longitudinal elongation was 80 g/cm and the stress at 100% transversal elongation was 40 g/cm, which results are shown in the following Table 1.

TABLE 1

| Items | Ex. 9 | Ex. 10 | Ex. 11 | Ex. 12 | Comp. Ex. 1 |
|---|---|---|---|---|---|
| Longitudinal Direction | | | | | |
| Stress at 100% Elongation (g/cm) | 100 | 160 | 80 | 60 | 80 |
| Transversal Direction | | | | | |
| Max. Stress (g/cm) | 1000 | 1000 | 1000 | 1000 | 40(*) |
| Max. Elongation (%) | 7 | 7 | 7 | 7 | — |
| Drape Property (cm) | 2 | 2 | 1 | 1 | 2 |
| Feeling | O | O | ⊕ | ⊕ | ⊕ |

Note: (*) The stress at 100% elongation

The controlled flexible elastic composite material according to the present invention have good controlled elasticity because both surfaces of a specific monoaxially oriented material are applied with flexible elastomer layers. Furthermore, by laminating at least two layers of specific stretched long fiber web and flexible elastomer layer, the laminate can have good feeling and proper elasticity. In addition, it is not elastic in its perpendicular direction and these controlled elastic composite materials have good mechanical strength.

With making the best use of the above characteristic features, the composite material of the present invention can be used widely for producing the fixing materials for the waist parts of the disposable diapers, clothes for working and surgical operation, caps for food works, garbage collecting and IC manufacturing process, fixings for gloves and shoe covers, and fixings for adhesive plasters and bandages.

What is claimed is:

1. A controlled elastic composite material comprising a flexible elastomeric layer and a first oriented layer, said first oriented layer formed of a thermoplastic resin selected from the group consisting of (a) a longitudinally monoaxially oriented reticular film; (b) a transversely monoaxially oriented reticular film; and (c) a plurality of monoaxially stretched or rolled tapes disposed in parallel.

2. A material in accordance with claim 1 comprising a second oriented layer formed of a thermoplastic material selected from the group consisting of (a), (b) and (c) wherein said first and said second oriented layers are disposed at an angle of from 10° to 80° relative to each other.

3. A material in accordance with claim 1 wherein said first oriented layer is a multilayered film formed by laminating a second thermoplastic resin layer on one or both surfaces of a first thermoplastic resin layer with the proviso that the melting point of said second thermoplastic resin is lower than that of said first thermoplastic resin.

4. A material in accordance with claim 1 wherein the ratio of orientation of said first oriented layer is in the range of 1.1 to 15.

5. A material in accordance with claim 2 wherein said second oriented layer is (c) and wherein said plurality of tapes are a pair of woven or non-woven fabrics.

6. A controlled elastic composite material comprising a flexible elastomeric layer and an oriented layer, said oriented layer comprising a first and a second oriented material crosswise laminated with each other at an intersecting angle of between 10° and 80°, said first and said second oriented materials being the same or different and selected from the group consisting of (a) a longitudinally monoaxially oriented reticular web; (b) a transversely monoaxially oriented reticular web; (c) a plurality of monoaxially stretched or rolled tapes which are disposed in parallel; and (d) a web which includes a plurality of fibers aligned in one direction and then stretched or rolled in that direction.

7. A material in accordance with claim 6 wherein said oriented layer is (c) and wherein said plurality of monoaxially stretched or rolled tapes disposed in parallel is a pair of woven or non-woven fabric webs.

8. A material in accordance with claim 6 wherein said monoaxially oriented material is selected from the group consisting of (a), (b) and (c) and wherein said materials are made from a multilayered film formed by laminating a second thermoplastic resin layer on one or both surfaces of a first thermoplastic resin layer with the proviso that the melting point of said second thermoplastic resin is lower than that of first thermoplastic resin.

9. A material in accordance with claim 6 wherein the ratio of orientation of said monoaxially oriented material is in the range of between 1.1 and 15 and wherein said monoaxially oriented material is selected from the group consisting of (a), (b) and (c).

10. A material in accordance with claim 6 wherein said monoaxially oriented material is (d) and wherein the ratio of stretching or rolling of said long fibers is in the range of between 5 and 20 and the fineness of said fibers is in the range of between 0.01 and 10 denier.

11. A material in accordance with claim 6 wherein said monoaxial material is (d) and wherein said fibers are composed of conjugate fiber consisting of a high melting point material and a low melting point material.

12. A controlled elastic composite material comprising a flexible elastomer layer and an oriented layer, said oriented layer including at least one monoaxially oriented fiber web having a plurality of fibers aligned in one direction and stretched or rolled in said direction.

13. A material in accordance with claim 12 wherein said oriented layer is formed by crosswise laminating a pair of monoaxially oriented fiber webs at an intersecting angle of between 10° and 80°.

14. A material in accordance with claim 12 wherein the ratio of stretching of said monoaxially oriented long fiber web is in the range of between 5 and 20 to produce a fineness in the range of between 0.01 and 10 denier.

15. A material in accordance with claim 12 wherein said monoaxially oriented fiber web is composed of conjugate fibers consisting of a high melting point material and a low melting point material.

* * * * *

UNITED STATES PATENT AND TRADEMARK OFFICE
CERTIFICATE OF CORRECTION

PATENT NO. : 5,702,798
DATED : December 30, 1997
INVENTOR(S) : Yukio Sugita, et al.

It is certified that error appears in the above-indentified patent and that said Letters Patent is hereby corrected as shown below:

Column 16, line 11, Claim 10: delete "long"

Column 16, line 28, Claim 14: delete "long"

Signed and Sealed this

Sixteenth Day of June, 1998

Attest:

BRUCE LEHMAN

Attesting Officer

Commissioner of Patents and Trademarks